United States Patent
Holm et al.

(10) Patent No.: US 9,975,113 B2
(45) Date of Patent: May 22, 2018

(54) PROCESS FOR THE CONVERSION OF SUGARS TO LACTIC ACID AND 2-HYDROXY-3-BUTENOIC ACID OR ESTERS THEREOF COMPRISING A METALLO-SILICATE MATERIAL AND A METAL ION

(71) Applicant: Haldor Topsoe A/S, Kgs. Lyngby (DK)

(72) Inventors: Martin Spangsberg Holm, Oxford (GB); Irantzu Sadaba Zubiri, Frederiksberg (DK); Søren Tolborg, Dyssegård (DE); Christian Mårup Osmundsen, Gentofte (DK); Esben Taarning, Frederiksberg (DK)

(73) Assignee: Haldor Topsoe A/S, Lyngby (DK)

(*) Notice: Subject to any disclaimer, the term of this patent is extended or adjusted under 35 U.S.C. 154(b) by 0 days. days.

(21) Appl. No.: 15/435,758

(22) Filed: Feb. 17, 2017

(65) Prior Publication Data

US 2017/0173570 A1    Jun. 22, 2017

Related U.S. Application Data

(63) Continuation of application No. 14/910,319, filed as application No. PCT/EP2014/067475 on Aug. 15, 2014, now Pat. No. 9,573,123.

(30) Foreign Application Priority Data

Aug. 20, 2013 (EP) .................................... 13181069

(51) Int. Cl.
C07C 69/66 (2006.01)
B01J 29/70 (2006.01)
(Continued)

(52) U.S. Cl.
CPC ......... *B01J 29/7057* (2013.01); *B01J 29/088* (2013.01); *B01J 29/7049* (2013.01);
(Continued)

(58) Field of Classification Search
CPC .......................... B01J 29/7057; B01J 29/088
(Continued)

(56) References Cited

U.S. PATENT DOCUMENTS 4,933,161 A    6/1990  Vaughan et al.
6,306,364 B1  10/2001  Valencia et al.
(Continued)

FOREIGN PATENT DOCUMENTS

CN    103058869 A    4/2013
EP    2 184 270 B1   2/2013
(Continued)

OTHER PUBLICATIONS

Qiang Guo et al: "Highly Active and Recyclable Sn—MWW Zeolite Catalyst for Sugar Conversion to Methyl Lactate and Lactic Acid", Chemsuschem, vol. 6, No. 8, 17 Jun. 2013 (Jun. 17, 2013), pp. 1352-1356.*
(Continued)

*Primary Examiner* — Deborah D Carr
(74) *Attorney, Agent, or Firm* — Blank Rome LLP

(57) ABSTRACT

A process for the preparation of lactic acid and 2-hydroxy-3-butenoic acid or esters thereof from a sugar in the presence of a metallo-silicate material, a metal ion and a solvent, wherein the metal ion is selected from one or more of the group consisting of potassium ions, sodium ions, lithium ions, rubidium ions and caesium ions.

22 Claims, 2 Drawing Sheets

(51) Int. Cl.
  *C07C 67/00* (2006.01)
  *B01J 29/08* (2006.01)
  *B01J 37/04* (2006.01)
  *B01J 37/08* (2006.01)
  *B01J 37/10* (2006.01)

(52) U.S. Cl.
  CPC ............... *B01J 37/04* (2013.01); *B01J 37/08* (2013.01); *B01J 37/10* (2013.01); *C07C 67/00* (2013.01); *B01J 2229/16* (2013.01); *Y02P 20/582* (2015.11)

(58) Field of Classification Search
  USPC ......................................................... 560/179
  See application file for complete search history.

(56) References Cited

U.S. PATENT DOCUMENTS

| | | |
|---|---|---|
| 2011/0212187 A1 | 9/2011 | Rabasse et al. |
| 2013/0204036 A1 | 8/2013 | Tominaga et al. |

FOREIGN PATENT DOCUMENTS

| | | |
|---|---|---|
| EP | 2 606 968 A2 | 6/2013 |
| WO | WO 2011/125882 A1 | 10/2011 |

OTHER PUBLICATIONS

S. Tolborg et al., "Tin-containing Silicates: Alkali Salts Improve Methyl Lactate Yield from Sugars", ChemSusChem 2015, vol. 8, pp. 613-617.
S. Tolborg et al., "Tin-containing Silicates: Alkali Salts Improve Methyl Lactate Yield from Sugars", ChemSusChem, 2015, pp. 1-13.
P. Dapsens et al., "Highly Selective Lewis Acid Sites in Desilicated MFI Zeolites for Dihydroxyacetone Isomerization to Lactic Acid", Chemsuschem, vol. 6, No. 5, Apr. 3, 2013, pp. 1-19.
C.B. Rasrendra et al., "Catalytic Conversion of Dihydroxyacetone to Lactic Acid Using Metal Salts in Water", Chemsuschem, vol. 4, No. 6, May 20, 2011. (Abstract only).
R. Bermejo-Deval et al., "Metalloenzyme-Like Catalyzed Isomerizations of Sugars by Lewis Acid Zeolites", PNAS, vol. 109, No. 25, Jun. 19, 2012, pp. 9727-9732.
Q. Guo et al., "Highly Active and Recyclable Sn—MWW Zeolite Catalyst for Sugar Conversion to Methyl Lactate and Lactic Acid", Chemsuschem, vol. 6, No. 8, Jun. 17, 2013 (Jun. 17, 2013), pp. 1352-1356).
C. Hammond et al., "Simple and Scalable Preparation of Highly Active Lewis Acidic Sn-β", Angewandte Chemie International Edition, vol. 51, No. 47, Nov. 19, 2012, pp. 11736-11739.

* cited by examiner

PROCESS FOR THE CONVERSION OF SUGARS TO LACTIC ACID AND 2-HYDROXY-3-BUTENOIC ACID OR ESTERS THEREOF COMPRISING A METALLO-SILICATE MATERIAL AND A METAL ION

The present invention relates to a novel process for the preparation of lactic acid and 2-hydroxy-3-butenoic acid or esters thereof from sugars in the presence of one or more metallo-silicate materials and one or more metal ions.

BACKGROUND

Carbohydrates represent the largest fraction of biomass and various strategies for their efficient use as a feedstock for commercial chemicals are being established. Biomass is of particular interest due to its potential for supplementing, and ultimately replacing, petroleum. One such commercial chemical obtainable from biomass is lactic acid; a lactic acid derivative, methyl lactate, is a convenient building block towards renewable and biodegradable solvents and polymers.

Lactic acid derivatives, in particular esters of lactic acid, may be obtained from sugars via a variety of reaction processes including biochemical (enzymatic fermentation) and synthetic (catalytic conversion). Particular attention has been focussed on synthetic routes as they provide a commercially and environmentally advantageous alternative to biochemical routes.

EP 2 184 270 B1 and Holm et. al. Science (2010), 328, p 602-605 disclose the conversion of common sugars to lactic acid derivatives wherein a heterogenous zeotype or zeolite catalyst is employed. Specifically, the conversion of glucose, sucrose or fructose to methyl lactate is disclosed. A variety of heterogenous Lewis-acid zeotype catalysts are identified as particularly active catalysts for this conversion. Sn-BEA has been identified as one of the most selective catalysts, as illustrated by the conversion of glucose, fructose and sucrone to methyl lactate with yields of 43, 44 and 68% respectively. There is a desire to further improve the percentage yield of useful products such as lactate esters and esters of 2-hydroxy-3-butenoic acid for this process.

In addition to the desire to improve the product yield of such processes using Sn-BEA as the catalyst, an increase in the product yield using alternative, easier to synthesize metallo-silicate catalysts would broaden the scope of catalysts suitable for industrially scaled processes. A particular advantage would be the application of an improved process and improved catalytic activity wherein the preparation of the catalyst itself is simplified and made suitable for industrial scale production.

Zeotype and zeolite catalysts comprising an active metal can be prepared by several methods including direct synthesis and post-synthesis preparations.

Direct synthesis methods, as described in EP 1 010 667 B1 and Chem Commun. (1997) pp 425-426, although very convenient for laboratory scale synthesis, may not be suitable for industrial scale production. These direct synthesis procedures experience practical and environmental limitations posed by: the use of reagents comprising fluoride such as hydrogen fluoride (HF); lengthy synthesis times; and the use of expensive organic templating agents which are difficult to reuse.

Recently, Hermans et al Angew. Chem. Int. Ed. (2012), 51, p 11736-11739, disclosed the preparation of Sn-BEA using a post synthesis process that does not require the use of a fluoride reagent. The post synthesis process disclosed by Hermans comprises de-aluminating a commercially available zeolite (Al-BEA), physically mixing this de-aluminated zeolite with a tin salt, followed by calcination of the de-aluminated zeolite and tin salt mixture. A general post-synthesis preparation method should thus include a step of defect generation in the silica framework via de-alumination or other similar procedure, for example de-boronation; and the addition of tin (Sn) and calcination, which produces the incorporation of Sn in the silica structure.

The post-synthesis preparation process has the advantages of: a short synthesis time; the possibility that large amounts of active metal may be incorporated into the framework structures; and avoidance of the use of expensive organic templating and a reagent comprising fluoride. These advantages enable the process of preparing the Sn-BEA to be scalable and potentially suitable for industrial scale processes. A similar post-synthesis methodology has also been applied to the synthesis of Sn-MWW: Qiang et al. ChemSusChem [vol 6, issue 8, 1352-1356, August (2013)].

For industrial scale catalyst production, it is a significant advantage if the metallo-silicate catalysts can be prepared by a post synthesis process; however, so far reported, all catalysts prepared by the post synthesis process are poor catalysts for the conversion of C6 sugars to lactate esters and esters of 2-hydroxy-3-butenoic acid. Only low yields of the desirable esters are obtained. See Example 1 of the present application.

Therefore there is a desire to improve both the percentage yield of the process of preparing lactic acid and 2-hydroxy-3-butenoic acid or esters thereof from sugars, in particular wherein the preparation of the catalyst is industrially feasible. It would be an additional advantage if the improvement could also broaden the scope of active catalysts suitable for this process and for an industrial scale.

SUMMARY OF THE INVENTION

It has now been discovered that the presence of a metal ion, in particular an alkali earth metal ion and/or an alkali metal ion in the presence of a metallo-silicate material, can increase the percentage yield of lactic acid and 2-hydroxy-3-butenoic acid or esters thereof from sugars. Additionally, this improved process increases the activity of a variety of catalysts for this particular process.

It is particularly surprising that the presence of a metal ion, in particular an alkali metal ion or alkaline earth metal ion, improves the desired product yield of this reaction as several literature references disclose the detrimental effect of the presence of an alkali metal ion on the catalytic activity of TS-1 and Ti-BEA catalysts for oxidative catalytic reactions; or observe no change when added to Sn-BEA under conditions for the isomerisation of glucose to fructose. Bermejo-Deval et al [PNAS, June 19, vol 109, No 25, (2012)] and Khouw et al. J. Catal. 151, 77-86, (1995).

Additionally, it can be seen from Examples 13-20 of the present invention that specific concentrations of the metal ion provide improved yields of the desired products. Whilst not wishing the invention to be limited by these results, it can be observed that there may be specific ranges of metal ion concentrations that can be seen as an optimisation of the process conditions.

DETAILED DESCRIPTION OF THE PREFERRED EMBODIMENTS

Figure 1:
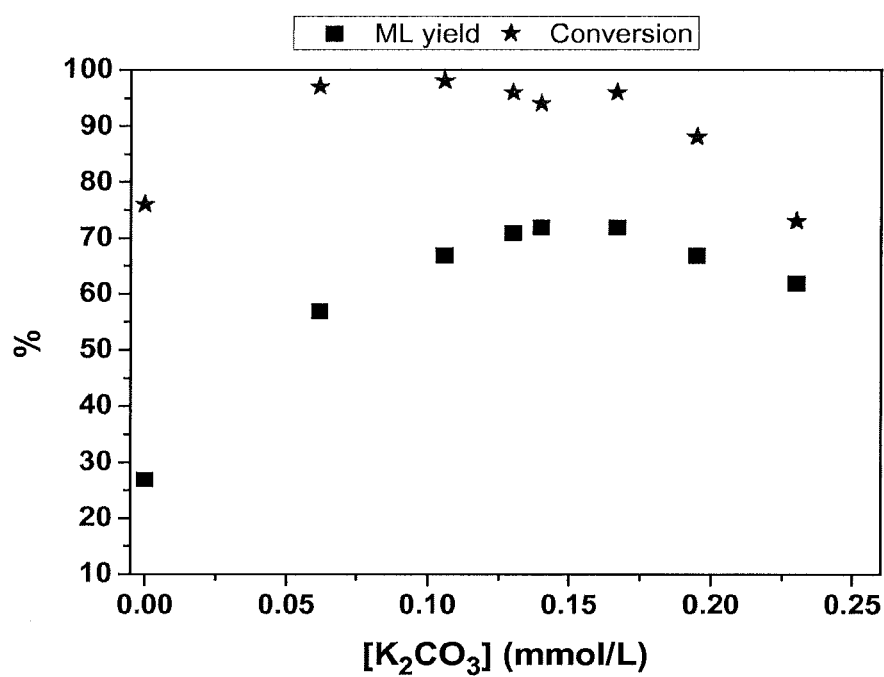
FIG. 1 shows a comparison of methyl lactate yield and conversion of sugar with variation of the metal ion concentration.

More specifically, the present invention relates to a process for the preparation of lactic acid and 2-hydroxy-3-butenoic acid or esters thereof from a sugar in the presence of a metallo-silicate material, a metal ion and a solvent, said process comprising contacting the sugar or an isomer or derivative thereof with a metallo-silicate material. The mechanism of the process of the present invention is not fully understood; it may therefore be possible that the process may comprise contacting the sugar or an isomer or derivative thereof with a metallo-silicate material and the metal ion.

Lactic acid and 2-hydroxy-3-butenoic acid or esters thereof means lactic acid and 2-hydroxy-3-butenoic acid or one or more esters of lactic acid, such as methyl or ethyl lactate, and one more esters of 2-hydroxy-3-butenoic acid, such as methyl or ethyl 2-hydroxy-3-butenoate.

Sugar relates to carbohydrates commonly found in biomass selected from one or more of the group consisting of glucose, fructose, mannose, sucrose, xylose, erythrose, erythrulose, threose and glycolaldehyde. The sugar may be in the form of an isomer of a sugar or a derivative of a sugar.

Metal ion relates to a metal ion originating from either the element itself or the salt of an alkali earth metal and/or an alkali metal. More specifically, the salt of the alkaline earth metal or alkali metal comprises at least one metal ion and at least one anion. Preferably the metal ion is selected from the group consisting of potassium, sodium, lithium, rubidium and caesium. Preferably the salt of the alkaline earth metal or alkali metal is selected from the group consisting of carbonate, nitrate, acetate, lactate, chloride, bromide and hydroxide. Even more preferably the metal ion originates from one or more salts of the alkaline earth metal or alkali metal selected from the group consisting of $K_2CO_3$, $KNO_3$, KCl, potassium acetate ($CH_3CO_2K$), potassium lactate ($CH_3CH(OH)CO_2K$), $Na_2CO_3$, $Li_2CO_3$, $Rb_2CO_3$.

The metal ion may be introduced into the process of the present invention either as a component of the metallo-silicate material, or independently as, for example, a solid or dissolved in a solvent.

Metallo-silicate material (also known as metallo-silicates, metallo-silicate composition or metallo-silicate catalyst) refers to one or more solid materials comprising silicon oxide and an active metal and/or metal oxide components, wherein the active metal and/or metal oxide components are incorporated into and/or grafted onto the surface of the silicon oxide structure (i.e. the silicon oxide structure comprises M—O—Si bonds). The silicon oxide structure is also known as a silicate. Metallo-silicate materials may display catalytic activity for the conversion of sugars to derivatives of lactic acid (e.g. esters of lactic acid or esters of 2-hydroxy-3-butenoic acid), lactic acid and 2-hydroxy-3-butenoic acid. Metallo-silicate materials may be crystalline or non-crystalline. Non-crystalline metallo-silicate materials include ordered mesoporous amorphous or other mesoporous amorphous forms. Crystalline microporous material includes zeolite materials and zeotype materials.

Zeolite materials are crystalline alumino-silicates with a microporous crystalline structure, according to Corma et al., Chem. Rev. 1995, 95 pp 559-614. The aluminum atoms of the zeolite material may be partly or fully substituted by an active metal; these materials fall within the class of zeotype materials. For the purpose of this application zeotype materials encompass zeolite materials. Preferably the metallo-silicate material is selected from one or more of the group consisting of zeotype materials and ordered mesoporous amorphous silicates.

Active metal relates to the metal that is incorporated into the metallo-silicate material. Active metal means one or more metals selected from the group consisting of Sn, Ti, Pb, Zr, Ge and Hf. Examples of active metal precursors may be tin chlorides or acetates, for example: $SnCl_4$; $SnCl_2$; Sn(IV) acetate; and Sn(II)acetate.

Preferably the active metal is selected from one or more of the group consisting of Ge, Sn, Pb, Ti, Zr and Hf. Preferably the zeotype material has a framework structure selected from the group consisting of BEA (Beta), MFI, FAU, MOR and FER. Preferably the ordered mesoporous amorphous silicate has a structure selected from the group consisting of MCM-41 and SBA-15. In a preferred embodiment, the metallo-silicate material is selected from the group consisting of Sn-BEA, Sn-MFI, Sn-FAU, Sn-MCM-41 and Sn-SBA-15.

A further aspect of the invention comprises the preparation of metallo-silicate materials. Metallo-silicate materials may be prepared by a variety of processes including hydrothermal crystallisation, as described in U.S. Pat. No. 6,306,364 B1; wherein a reaction mixture is prepared by combining reactive sources of tin, silicon an organic templating agent and water. Alternatively, a zeolite material may be modified and combined with tin, as described in the post synthesis process disclosed by Hermans et. Al., Angew. Chem. Int. Ed. (2012), 51, p 11736-11739. The post synthesis process disclosed by Hermans et al. comprises de-aluminating a commercially available zeolite catalyst (Al-BEA), physically mixing this de-aluminated zeolite catalyst with a tin (Sn) salt followed by calcination of the de-aluminated zeolite and tin (Sn) salt mixture.

A further aspect of the present invention is the use of a metallo-silicate material prepared by a post synthesis process. Post synthesis process means a process comprising preparing a material comprising framework defects and impregnating the material with an active metal or active metal and metal ion. The process for preparing a material comprising framework defects is the selective removal of one or more heteroatoms from a zeolite or zeotype material. The selective removal of one or more heteroatoms from a zeolite or zeotype material may be for example de-aluminating or de-boronating a zeolite or zeotype material. The material comprising framework defects is impregnated with an active metal, or an active metal and a metal ion.

The process for preparing metallo-silicate materials or metallo-silicate materials comprising a metal ion may comprise the steps:
 a. Providing one or more zeotype materials or mesoporous amorphous silicate materials.
 b. De-aluminating or de-boronating the material of step a.
 c. Impregnating or mechanically mixing the product of step b. with an active metal.
 d. Optionally adding a metal ion to step c.
 e. Optionally drying the product of step c or d.
 f. Calcining the product of steps c, d and e.

In a preferred embodiment step b. comprises heating the material of step a. in acidic conditions or exposing the material of step a. to steam and acidic conditions. In an embodiment of the invention the material of step b. is filtered, washed and dried. In an embodiment of the invention the material of step b. is filtered, washed and calcined. In a further preferred embodiment the material of step b. is filtered, washed, dried and calcined.

The heating of step b. may be at a temperature of between about 70 and 120° C., between 70° C. and 100° C., between about 70° C. and 90° C., between 70° C. and 90° C., preferably about 80° C. The heating may occur over a period of time between 2 and 6 hours, between about 11 and 13 hours, between 11 and 13 hours.

Acidic conditions as described in the preferred embodiments of step b. may be concentrated acid solutions. Preferably the acid is selected from the group consisting of $HNO_3$, $H_2SO_4$ and HCl.

All calcination steps are carried out between 400° C. and 600° C., between 500° C. and 600° C., between 520° C. and 580° C., preferably between about 540° C. and about 560° C. Calcination may occur over a period of time, for example between about 5 and 7 hours, between 5 and 7 hours.

The proper use and understanding of the term impregnation is self-explanatory and lies well within the ability of a person skilled in the art of catalyst, including metallo-silicate, preparation. Examples of impregnation techniques are provided in K. P. de Jong, Synthesis of Solid Catalysts, Wiley, 2009. ISBN: 978-3-527-32040-0.

A preferred embodiment of the impregnation of step c. is incipient wetness impregnation. A general example of the incipient wetness impregnation technique is provided in Campnanati et al., Catalysis Today 77 (2003) 299-314. Preferably, the impregnation comprises adding an aqueous solution of an active metal precursor to the solid of step b.

A further embodiment of the invention is the preparation of a metallo-silicate material wherein the products of steps d., e. and f. comprise a metal ion. The metal ion is introduced into the product by addition of a solution of the metal ion during the impregnation step of step c.

The present invention provides a process for the preparation of metallo-silicate materials and a process for the preparation of metallo-silicate materials comprising a metal ion (such as an alkaline earth metal ion or alkali metal ion).

The metallo-silicate materials prepared by post-synthesis treatment of silicates with an active metal by incipient wetness impregnation are a further aspect of the present invention. A preferred embodiment is a metallo-silicate material comprising a metal ion and prepared by a post synthesis process of the silicate with an active metal.

The metal ion may be introduced into the process of the present invention independently of the metallo-silicate material, for example by dissolving the metal ion in the reaction solvent. The metal ion may be dissolved in the reaction solution by adding the metal ion as a metal salt to the reaction solution or by dissolving the metal salt in a solvent and adding the dissolved metal salt to the reaction solution.

In a further embodiment of the invention, when any metallo-silicate material is used in conjunction with $K_2CO_3$ as metal ion source, the active metal to metal ion ratio may be between 1 and 20, preferably between 2 and 10.

In a further embodiment of the invention, when any Sn-BEA metallo-silicate material is used in conjunction with $K_2CO_3$ as metal ion source, the active metal to metal ion ratio may be between 1 and 20, preferably between 2 and 10. Any Sn-BEA metallo-silicate material means Sn-BEA or Sn-BEA comprising a metal ion.

In a further embodiment of the invention, when catalyst A (Sn-BEA) is used in conjunction with $K_2CO_3$ as metal ion source, the active metal to metal ion ratio may be between 1 and 20, preferably between 2 and 10, preferably between 3 and 7, more preferably between 3 and 6.

In a further embodiment of the invention, when catalyst A" (Sn-BEA) is used in conjunction with $K_2CO_3$ as metal ion source, the active metal to metal ion ratio may be between 1 and 20, between 2 and 16, between 5 and 9.5.

In a further embodiment of the invention, when catalyst A is used in conjunction with $K_2CO_3$ as metal ion source, the initial concentration of the metal ion in the solvent is less than 0.5 mmol/L, equal to or less than 0.23, between 0.05 mmol/L and 0.25 mmol/L, between 0.06 mmol/L and 0.2 mmol/L, between 0.13 mmol/L and 0.17 mmol/L.

The reaction vessel/solution that is used in the process is heated to a temperature of less than 200° C., preferably the vessel is heated to between 100° C. and 180° C.; more preferably the vessel is heated to between 120° C. and 170° C., even more preferably between 140° C. and 160° C.

In a further embodiment of the invention the solvent is selected from one or more of the group consisting of methanol, ethanol, 1-propanol, 1-butanol and water.

In a further embodiment of the invention the percentage yield of lactate from sugar is equal to or greater than 50 wt, equal to or greater than 55 wt %, equal to or greater than 60 wt %, equal to or greater than 65 wt %, equal to or greater than 70 wt %, equal to or greater than 75 wt %.

In a further embodiment of the invention the percentage yield of methyl lactate from sugar is equal to or greater than 50 wt %, equal to or greater than 55 wt %, equal to or greater than 60 wt %, equal to or greater than 65 wt, equal to or greater than 69 wt %, equal to or greater than 70 wt %, equal to or greater than 75 wt %.

Additionally, the process for the preparation of lactic acid and 2-hydroxy-3-butenoic acid or esters thereof of the current invention is suitable for both batch scale reactions and continuous flow reactions.

EXAMPLES

The following examples are provided to illustrate the invention. The examples shall not be construed as a limitation of how the invention may be practised.

Method A: Method for Preparing Methyl Lactate from Sucrose [16 Hour Reaction Duration].

A stainless steel pressure vessel (40 cc, Swagelok) is charged with a methanol (15.0 g; Sigma-Aldrich, >99.8%) solution of the metal salt (metal ion source), sucrose (0.450 g; Fluka, >99.0%) and catalyst (0.150 g). The reactor is closed and heated to 160° C. under stirring (700 rpm). The reaction is continued at 160° C. for 16 h and after this period, the reaction is quenched by submerging the vessel in cold water. Samples from the reaction vessel are filtered and analysed by HPLC (Agilent 1200, Biorad Aminex HPX-87H column at 65° C., 0.05 M $H_2SO_4$, 0.6 ml min$^{-1}$) to quantify unconverted hexoses and dihydroxyacetone (DHA), glyceraldehyde (GLA); and GC (Agilent 7890 with a Phenomenex Solgelwax column) was used to quantity: methyl lactate (ML), methyl vinylglycolate (MVG, methyl 2-hydroxy-3-butenoate) and glycolaldehyde dimethylacetal (GADMA).

The amount of metal salt is provided for all Examples via the column entitled: 'initial metal ion concentration in methanol'.

Method B: Method for Preparing Methyl Lactate from Sucrose [4 Hour Reaction Duration].

A method for preparing methyl lactate from sucrose as described in Method A, with the exception that the reaction duration is 4 hours.

Catalyst Preparation:

Catalyst A [Sn-BEA (Si/Sn=125)]:

Commercial zeolite Beta (Zeolyst, Si/Al 12.5, ammonium form) is calcined (550° C. for 6 h) to obtain the zeolite Beta H form (de-aluminated form) and treated with 10 grams of concentrated nitric acid (Sigma-Aldrich, 65%) per gram of zeolite Beta powder for 12 h at 80° C. The resulting solid is filtered, washed with ample water and calcined (550° C. for 6 h) to obtain the de-aluminated Beta solid.

The de-aluminated Beta solid is impregnated with Sn by incipient wetness methodology with a Sn/Si ratio of 125 using the following method: tin (II) chloride (0.128 g, Sigma-Aldrich, 98%) is dissolved in water (5.75 mL) and added to the de-aluminated Beta (5 g). After impregnation the samples are dried 12 h at 110° C. and calcined (550° C. for 6 h).

Catalyst A' [Sn-BEA (Si/Sn=125) Comprising a Metal Ion]:

Sn-BEA (Si/Sn=125) comprising a metal ion is prepared according to a modification of the previous procedure (preparation of Catalyst A). Commercial zeolite Beta (Zeolyst, Si/Al 12.5, ammonium form) is calcined (550° C. for 6 h) to obtain the H form (de-Aluminated form) and treated with 10 g of concentrated nitric acid (Sigma-Aldrich, 65%) per gram of zeolite Beta powder for 12 h at 80° C. The resulting solid is filtered, washed with ample water and calcined (550° C. for 6 h) to obtain a de-aluminated Beta solid.

The de-aluminated Beta solid is impregnated with Sn and potassium ions by incipient wetness methodology to obtain a Sn/Si ratio of 125 using the following method: tin (II) chloride (0.125 g, Sigma-Aldrich, 98%) is dissolved in a $K_2CO_3$ solution (5.75 mL of 0.0015 M in water) and added to the de-aluminated Beta (5 g). After impregnation the samples are dried 12 h at 110° C. and calcined (550° C. for 6 h).

Catalyst A":

Sn-BEA (Si/Sn=200) is prepared according to a modification of the route described in U.S. Pat. No. 6,306,364 B1. TEOS (30.6 g; Aldrich, 98%) is added to TEAOH (33.1 g; Sigma-Aldrich, 35% in water) under stirring, forming a two-phase system. After 60-90 min, one phase is obtained. Tin(IV) chloride pentahydrate (0.26 g; $SnCl_4 \cdot 5H_2O$, Aldrich, 98%) is dissolved in water (2.0 mL) and added dropwise. The solution is then left for several hours under stirring until a viscous gel was formed. The gel is then mineralized by the addition of HF (3.1 g; Fluka, 47-51%) in demineralized water (1.6 g). A suspension of de-aluminated seeds of Sn-BEA (0.36 g) in demineralized water (3.0 g) is added, followed by manual mixing. The gel is homogenized and transferred to a Teflon-lined container and placed in a stainless steel autoclave and heated statically at 140° C. for 14 days. The solid is recovered by filtration and washed with ample amounts of deionized water, followed by drying overnight at 80° C. in air. The synthesis is finalized by removing the organic template by heating the sample at 2° C./min to 550° C. in static air and maintaining this temperature for 6 h.

Catalyst B [Sn—Y]:

Commercial zeolite Y (Zeolyst, Si/Al 50, hydrogen form) is treated with 10 grams of concentrated nitric acid (Sigma-Aldrich, 65%) per gram of zeolite Beta powder for 12 h at 80° C. The resulting solid is filtered, washed with ample water and calcined (550° C. for 6 h) to obtain de-aluminated Y.

The de-aluminated Y solid is impregnated with Sn by incipient wetness methodology with a Sn/Si ratio of 125 using the following method: tin (II) chloride (0.124 g, Sigma-Aldrich, 98%) is dissolved in water (7.5 mL) and added to de-aluminated Y (5 g). After impregnation the samples are dried for 12 h at 110° C. and calcined (550° C. for 6 h).

Catalyst C [Sn-MCM-41]:

Sn-MCM-41 is prepared according to the method described by Li, L. et al. [Green Chem. 2011, 13, 1175-1181]. In a typical synthesis hexadecyltrimethylammonium bromide (13.0 g; CTABr, Sigma>98%) is dissolved in water (38.0 g). Tetramethylammonium silicate (26.4 g; TMAS, Aldrich, 15-20 wt % in water) is added slowly. The mixture is stirred for 50 min.

Tin(IV) chloride pentahydrate ($SnCl_4 \cdot 5H_2O$; 0.179 g; Aldrich, 98%) and HCl (0.605 g; Sigma-Aldrich, 37 wt %) are dissolved in water (2.1 g) and added slowly to the solution. The resulting mixture is stirred for 1.5 h and TEOS (12.2 g) is added. The mixture is stirred for another 3 h and transferred to a Teflon lined autoclave and heated to 140 C for 15 h. The solid is recovered by filtration and washed with ample amounts of deionized water, followed by drying overnight at 80° C. in air. The synthesis was finalized by removing the organic template by heating the sample at 2° C./min to 550° C. in static air and maintaining this temperature for 6 h.

Examples 1-6

Method A (16 h reaction) was followed using Catalyst A and the metal salt (metal ion source). Results are provided in Table 1.

TABLE 1

| Ex | Metal salt [Metal ion source] | Initial metal ion concentration in methanol (mmol/L) [M+] | Ratio of active metal to metal ion | Percentage Yield of methyl lactate | Total Conversion of Hexose Sugars |
|---|---|---|---|---|---|
| 1 | — | — | — | 27 | 76 |
| 2 | $K_2CO_3$ | 0.13 | 5 | 72 | 96 |
| 3 | $KNO_3$ | 0.13 | 5 | 23 | 93 |
| 4 | KCl | 0.13 | 5 | 28 | 95 |
| 5 | Potassium Acetate | 0.13 | 5 | 39 | 95 |
| 6 | Potassium lactate | 0.13 | 5 | 46 | 95 |

Examples 7-10

Method A (16 h reaction) was followed using Catalyst A and the metal salt (metal ion source). Results are provided in Table 2.

TABLE 2

| Ex | Metal salt [Metal ion source] | Initial metal ion concentration in methanol (mmol/L) [M+] | Ratio of active metal to metal ion | Percentage Yield of methyl lactate | Total Conversion of Hexose Sugars |
|---|---|---|---|---|---|
| 2 | $K_2CO_3$ | 0.13 | 5 | 72 | 96 |
| 7 | $Li_2CO_3$ | 0.13 | 5 | 59 | 84 |
| 8 | $Na_2CO_3$ | 0.13 | 5 | 72 | 97 |
| 9 | $Rb_2CO_3$ | 0.13 | 5 | 67 | 98 |
| 10 | $CaCO_3$ | 0.13 | 5 | 18 | 94 |

Examples 11-17

Method A (16 h reaction) was followed varying the type of metallo-silicate material. The metal salt used as a source of metal ions is $K_2CO_3$. Results are provided in Table 3.

TABLE 3

| Ex | Catalyst | Initial metal ion concentration in methanol (mmol/L) [M+] | Ratio of active metal to metal ion | Percentage Yield of methyl lactate | Total Conversion of Hexose Sugars |
|---|---|---|---|---|---|
| 1 | A | — | — | 27 | 76 |
| 2 | A | 0.13 | 5 | 72 | 96 |
| 11 | A' | — | 7 | 71 | 96 |
| 12 | A" | — | — | 26 | 93 |
| 13 | A" | 0.13 | 3 | 58 | 73 |
| 14 | B | — | — | 11 | 67 |
| 15 | B | 0.13 | 5 | 67 | 97 |
| 16 | C | — | — | 20 | 79 |
| 17 | C | 0.13 | 3 | 52 | 89 |

Examples 18-23

Method A (16 h reaction) was followed varying the concentration of the metal ion; the metal salt used as a metal ion source is $K_2CO_3$. Catalyst A is used. Results are provided in Table 4.

TABLE 4

| Ex | Initial metal ion concentration in methanol (mmol/L) [M+] | Ratio of active metal to metal ion | Percentage Yield of methyl lactate | Total Conversion of Hexose Sugars |
|---|---|---|---|---|
| 1 | 0 | — | 27 | 76 |
| 18 | 0.06 | 10.3 | 57 | 97 |
| 19 | 0.11 | 6.2 | 67 | 98 |
| 2 | 0.13 | 5.0 | 72 | 96 |
| 20 | 0.14 | 4.2 | 72 | 94 |
| 21 | 0.17 | 3.9 | 72 | 96 |
| 22 | 0.20 | 3.2 | 67 | 88 |
| 23 | 0.23 | 2.6 | 62 | 73 |

Examples 24-28

Method A (16 h reaction) was followed varying the concentration of the metal ion; the metal salt used as a metal ion source is $K_2CO_3$. Catalyst A" is used. Results are provided in Table 5.

TABLE 5

| Ex | Initial metal ion concentration in methanol (mmol/L) [M+] | Ratio of active metal to metal ion | Percentage Yield of methyl lactate | Total Conversion of Hexose Sugars |
|---|---|---|---|---|
| 12 | 0 | — | 26 | 93 |
| 24 | 0.03 | 16.0 | 57 | 97 |
| 25 | 0.045 | 9.0 | 67 | 93 |
| 26 | 0.055 | 7.0 | 69 | 94 |
| 27 | 0.065 | 6.5 | 75 | 93 |
| 28 | 0.1 | 4.5 | 59 | 78 |
| 13 | 0.13 | 3 | 58 | 73 |

Examples 29-33

Method B (4 h reaction) was followed varying the concentration of the metal ion; the metal salt used as a metal ion source is $K_2CO_3$. Catalyst B is used. Results are provided in Table 6.

TABLE 6

| Ex | Initial metal ion concentration in methanol (mmol/L) [M+] | Ratio of active metal to metal ion | Percentage Yield of methyl lactate | Total Conversion of Hexose Sugars |
|---|---|---|---|---|
| 14 | 0 | — | 11 | 67 |
| 29 | 0.07 | 7.7 | 33 | |
| 30 | 0.10 | 6.3 | 45 | |
| 31 | 0.13 | 5.0 | 56 | |
| 32 | 0.17 | 4.0 | 44 | |
| 33 | 0.20 | 3.3 | 45 | |

Key:
[M+]=Metal ion concentration in the reaction solution.
[$K_2CO_3$]=Metal ion concentration; in this Example the metal ion is potassium originating from $K_2CO_3$.
%=Percentage Yield of methyl lactate
Conversion of Sugar=Total Conversion of Sugar Starting Material.

FIG. 1: Examples 1, 2 and 18 to 23: Comparison of methyl lactate yield and conversion of sugar with variation of the metal ion concentration. Method A was followed using Catalyst A.

Figure 2:
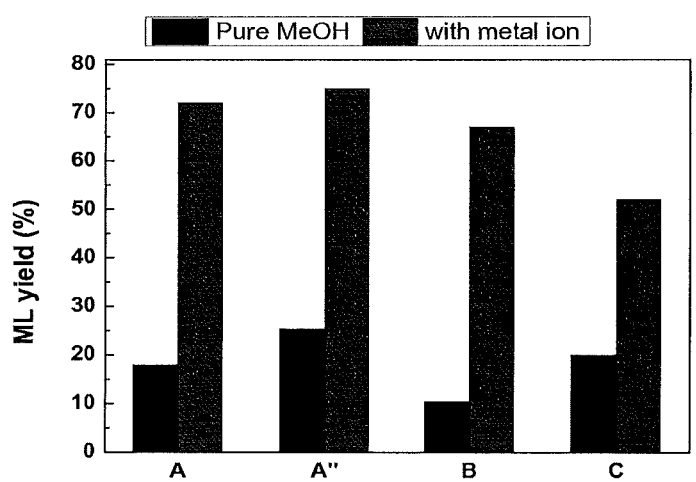
FIG. 2 shows a comparison of methyl lactate yield using various catalysts, where the reaction is carried out in pure methanol (i.e. without a metal ion), or methanol and a metal ion (i.e. potassium ions).

FIG. 2: Examples 1, 2 and 12 to 17: Comparison of methyl lactate yield prepared via Method A using catalysts A, A", B and C; wherein the reaction is carried out in pure methanol (i.e. without a metal ion), or methanol and a metal ion (i.e. potassium ions). Methyl lactate yield is significantly increased by the addition of a metal ion (i.e. potassium ions).

What is claimed is:

1. A metallo-silicate material suitable for preparing lactic acid and 2-hydroxy-3-butenoic acid or esters thereof from a sugar, which metallo-silicate material comprises a metal ion selected from the group consisting of alkaline earth metal ions and alkali metal ions.

2. The metallo-silicate material according to claim 1, wherein the metallo-silicate material comprises a silicon oxide structure and an active metal and wherein the silicon oxide structure comprises M-O—Si bonds.

3. The metallo-silicate material according to claim 1, wherein the metallo-silicate material is a zeotype material.

4. The metallo-silicate material according to claim 1, wherein the metallo-silicate material is a non-crystalline material.

5. The metallo-silicate material according to claim 1, comprising a framework structure selected from the group consisting of BEA, MFI, FAU, MOR, FER, MCM-41 and SBA-15.

6. The metallo-silicate material according to claim 2, wherein the active metal is selected from one or more of the group consisting of Sn, Ti, Pb, Zr, Ge and Hf.

7. The metallo-silicate material according to claim 1, selected from the group consisting of Sn-BEA, Sn-MFI, Sn-FAU, Sn-MOR, Sn-FER, Sn-MCM-41 and Sn-SBA-15.

8. The metallo-silicate material according to claim 2, wherein the atomic ratio of silicon to active metal is in the range of from 50:1 to 1:400.

9. The metallo-silicate material according to claim 2, wherein the atomic ratio of silicon to active metal is in the range of from 75:1 to 1:300.

10. The metallo-silicate material according to claim 2, wherein the active metal is Sn and wherein the atomic ratio of silicon to Sn is in the range of from 75:1 to 1:300.

11. The metallo-silicate material according to claim 1, wherein the metal ion is selected from one or more of the group consisting of potassium ions, sodium ions, lithium ions, rubidium ions and caesium ions.

12. The metallo-silicate material according to claim 2, wherein the active metal to metal ion ratio is in the range of from 1:1 to 100:1.

13. A process for preparing a metallo-silicate material comprising a metal ion according to claim 1, comprising:
    a. Mixing a reactive source of silicon, a reactive source the active metal and a reactive source of the metal ion;
    b. Crystallizing under hydrothermal conditions to obtain the metallo-silicate material comprising the metal ion.

14. The process according to claim 13, wherein step b) is conducted at a temperature in the range of from 100-200 grC.

15. The process according to claim 13, wherein the reactive source of silicon is selected from TEOS (tetraethyl orthosilicate), TMOS (tetramethyl orthosilicate), tetramethylammonium silicate, sodium silicate, colloidal silica sols, fumed silica and precipitated silica.

16. The process according to claim 13, wherein the reactive source of active metal is selected from tin (II) chloride, tin (IV) chloride pentahydrate, tin (II) acetylacetonate, tin (II) bromide, tin (IV) bromide, tin (II) acetate, tin (IV) acetate, tin (II) oxalate, tin (IV) butoxide, zirconium (IV) acetylacetonate, zirconium (IV) acetate, zirconium (IV) chloride, zirconium (IV) oxynitrate hydrate, zirconium (IV) ethoxide, zirconium (IV) propoxide, zirconium (IV) butoxide, zirconium (IV) isopropoxide, zirconium (IV) acetate hydroxide, titanium (IV) isopropoxide, titanium (IV) butoxide, titanium (IV) oxide and titanium (IV) hydroxide.

17. The process according to claim 13, wherein the reactive source of metal ion is selected from the group consisting of $K_2CO_3$, $KNO_3$, KCl, potassium acetate ($CH_3CO_2K$), potassium lactate ($CH_3CH(OH)CO_2K$), $Na_2CO_3$, $Li_2CO_3$ and $Rb_2CO_3$.

18. A process for preparing a metallo-silicate material from a zeotype material comprising a metal ion, comprising the steps of:
    a. Providing one or more zeotype materials; then
    b. De-aluminating or de-boronating the material of step a) to obtain a framework defective material; then
    c. Adding a reactive source of active metal to the framework defective material; and in any order
    d. Calcining; and
    e. Adding a reactive source of the metal ion.

19. The process according to claim 18, wherein step d of calcining is conducted at a temperature in the range of from 300 to 600 grC.

20. The process according to claim 18, wherein the reactive source of active metal is selected from tin (II) chloride, tin (IV) chloride pentahydrate, tin (II) acetylacetonate, tin (II) bromide, tin (IV) bromide, tin (II) acetate, tin (IV) acetate, tin (II) oxalate, tin (IV) butoxide, zirconium (IV) acetylacetonate, zirconium (IV) acetate, zirconium (IV) chloride, zirconium (IV) oxynitrate hydrate, zirconium (IV) ethoxide, zirconium (IV) propoxide, zirconium (IV) butoxide, zirconium (IV) isopropoxide, zirconium (IV) acetate hydroxide, titanium (IV) isopropoxide, titanium (IV) butoxide, titanium (IV) oxide and titanium (IV) hydroxide.

21. The process according to claim 18, wherein the reactive source of metal ion is selected from the group consisting of $K_2CO_3$, $KNO_3$, KCl, potassium acetate ($CH_3CO_2K$), potassium lactate ($CH_3CH(OH)CO_2K$), $Na_2CO_3$, $Li_2CO_3$ and $Rb_2CO_3$.

22. Use of the catalyst according to claim 1 for preparation of lactic acid and/or 2-hydroxy-3-butenoic acid or esters thereof from a sugar.

* * * * *